United States Patent
Mayayo Falo

(10) Patent No.: US 11,147,882 B2
(45) Date of Patent: Oct. 19, 2021

(54) METHOD FOR PRESERVING AND STABILIZING PROTEINS FOR FORMULATIONS OF SANITARY, PHARMACEUTICAL AND COSMETIC PRODUCTS

(71) Applicant: SANI-RED, S.L., Barcelona (ES)

(72) Inventor: Teodoro Mayayo Falo, Barcelona (ES)

( * ) Notice: Subject to any disclaimer, the term of this patent is extended or adjusted under 35 U.S.C. 154(b) by 0 days.

(21) Appl. No.: 16/411,782

(22) Filed: May 14, 2019

(65) Prior Publication Data
US 2019/0290770 A1    Sep. 26, 2019

Related U.S. Application Data

(63) Continuation-in-part of application No. 15/855,338, filed on Dec. 27, 2017, now abandoned, which is a continuation-in-part of application No. 14/759,320, filed as application No. PCT/ES2014/000151 on Sep. 23, 2014, now abandoned.

(30) Foreign Application Priority Data

Sep. 23, 2013 (ES) ................ ES201331394

(51) Int. Cl.
| | |
|---|---|
| *A61K 47/44* | (2017.01) |
| *A61K 38/18* | (2006.01) |
| *A61K 47/22* | (2006.01) |
| *A61K 47/12* | (2006.01) |
| *A61K 47/14* | (2017.01) |
| *A61K 47/18* | (2017.01) |
| *A61K 47/10* | (2017.01) |

(52) U.S. Cl.
CPC .......... *A61K 47/44* (2013.01); *A61K 38/1808* (2013.01); *A61K 38/1825* (2013.01); *A61K 38/1841* (2013.01); *A61K 47/10* (2013.01); *A61K 47/12* (2013.01); *A61K 47/14* (2013.01); *A61K 47/18* (2013.01); *A61K 47/22* (2013.01)

(58) Field of Classification Search
None
See application file for complete search history.

(56) References Cited

PUBLICATIONS

Chang, Byeong S. etal. (2002) "Practical Approaches to Protein Formulation Development" Chapter 1, In, Rational Design of Stable Protein Formulations: Theory and Practice, J. F. Carpenter etal. (eds.), Springer US, pp. 1-25.*

Krishnamurth, Rajesh et al. (2002) "The stability factor: importance in formulation development", Current Pharmaceutical Biotechnology, vol. 3, Issue 4, pp. 361-371.

Chi, Eva Y. et al. (2003) "Physical Stability of Proteins in Aqueous Solution: Mechanism and Driving Forces in Nonnative Protein Aggregation", Abstract Pharmaceutical Research, vol. 20, No. 9, pp. 1325-1326.

* cited by examiner

*Primary Examiner* — Marianne P Allen

(57) ABSTRACT

A method for preserving and stabilizing proteins includes the steps of forming an anhydrous medium having oily phase components having hydrophilic residues, and dispersing the proteins into the anhydrous medium under ambient pressure and temperature conditions so that the proteins are incorporated into the anhydrous medium so as to maintain an active formation of the proteins.

1 Claim, 5 Drawing Sheets

Control　　　　　　　Aged　　　　　　　Current

Before treatment

After treatment

METHOD FOR PRESERVING AND STABILIZING PROTEINS FOR FORMULATIONS OF SANITARY, PHARMACEUTICAL AND COSMETIC PRODUCTS

CROSS-REFERENCE TO RELATED APPLICATIONS

The present application is a continuation-in-part of U.S. patent application Ser. No. 15/855,338, filed on Dec. 27, 2017, presently pending. Application Ser. No. 15/855,338 is a continuation-in-part of U.S. patent application Ser. No. 14/759,320, filed on Oct. 14, 2015, now abandoned.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to a method for preserving and stabilizing proteins. This method of preserving and stabilizing proteins relates to the industrial development of formulations of sanitary, pharmaceutical and cosmetic products. Additionally, the present the present invention relates to the industrial chemical sector dedicated to the manufacture of pharmaceutical and cosmetic products, and in particular those intended to preserve growth factors.

2. Description of Related Art Including Information Disclosed Under 37 CFR 1.97 and 37 CFR 1.98

Currently the stability in proteins has attracted considerable interest in the chemical, pharmaceutical and cosmetic field. Proteins are used as active substances of numerous treatments in diseases such as diabetes, cancer, haemophilia, myocardial infarction, just to cite some pathologies [Krishnamurthy and Manning, 2002]. Note that the use of protein structures such as growth factors, e.g. the EGF, aroused a great interest in the cosmetic industry in recent years. So, if a protein cannot be properly stabilized, it may lose its native structure with consequent loss of its biological activity [Krishnamurthy and Manning, 2002].

The problem is that the protein stabilization is particularly difficult since they are very susceptible to degradation phenomena: physical, chemical and enzymatic. Chemical degradation is related to deamination, oxidation, reduction, hydrolysis processes and chemical interactions such as disulfide bond interactions. Physical degradation includes surface adsorption, aggregation, dissociation, denaturation, and photolysis processes. In addition, there are factors that influence the aggregation of proteins related to the properties of the dispersion medium, such as temperature (related to the thermodynamics and kinetics of transformation of the structural protein conformation), pH (related to interactions of positive or negative charges with the protein residues), ionic strength (related to salts and their concentration to interact with charged groups) and surfactants (related to conformational thermodynamic stability) [Chi et al., 2003].

The formulation scientist's key goal is to achieve long-term stability of a drug compound. In the case of protein drugs, stabilization means not only maintaining the native chemical structure, but the native secondary and higher order structures necessary for biological activity. Without the ability to stabilize native protein structures, even the most efficacious protein therapeutics will fail to make viable drug products.

The EGF normally has a half-life of 7 hours like scientific article say: (The evaluation of stability of recombinant human epidermal growth factor in burn-injured pigs, Chih-Hui Yang, Yaw-Bin Huang, Pao-Chu Wu, Yi-Hung Tsai, Process Biochemistry Volume 40, Issue 5, April 2005, Pages 1661-1665. Based on the Arrhenius equation, the half-life of rhEGF at 25° C. was 6.93 h.) The calculated half-life ranged from 3.65 to 6.93 h over a pH range of 3.0-8.0 at 25 8 C. When the temperature was raised to 37 8C, the halflife diminished significantly from 6.93 to 3.47 h at pH 7.2.

There are technological processes to ensure that proteins remain for longer period of time with its native conformation, said processes can be carried out by physical processes such as freezing (below −10° C.) or lyophilisation (for the elimination of the humidity present in an aqueous solution of protein), however, even the products obtained by these methods suffer from degradation; or chemical processes through the addition of co-solvents may be carried out [Chang and Pikal, 2009].

The EGF was the first polypeptide isolated and characterized as a growth factor. It has a biological activity related to its native structure capable of stimulating the proliferation of keratinocytes and fibroblasts (with the consequent formation of collagen), induces angiogenesis (formation of new vessels) and performs subsequent vascularisation of the area where it is applied. These properties promote the appearance of new skin with a considerable thick, restoring its elasticity and firmness, thus diminishing the unwanted effects of cellular oxidation and therefore resulting in the elimination of wrinkles [Tang et al., 1994]. Such growth factor has begun to use recently in topical formulations, where very good results have been obtained related to tissue regeneration, the acceleration in the healing of burns, treatment of keloid, acne and stretch marks, even improving outcomes of treatments of surgical type, promotion of the consolidation of skin grafts as well as the post-peeling application. However, said proteins are increasingly used in the pharmaceutical and cosmetic industry, but have not been used massively due to its high prices and their difficult stabilisation [Schouest et al., 2012].

Fibroblast growth factor (bFGF) is a growth factor that acts to increase the mitotic activity index and DNA synthesis, facilitating the proliferation of various precursor cells, such as chondroblasts, collagenoblasts, and osteoblasts, etc., that form the body's fibrous, connective, and support tissues. It contributes to wound healing, haematopoiesis, angiogenesis, or the embryonic development. To this end, they perform very different functions: a) they contribute to the re-epithelialisation of the tissues damaged during healing; b) they have blood vessel formation inducing-activity; c) they are involved in processes for differentiation of the blood cell lines; and, d) they are involved in the differentiation of skeletal and cardiac muscle, the maturation of the lungs and the specification of the hepatocytes from endoderm cells. The object of the present invention is, therefore, the development of a new method for preserving and stabilising proteins, which can be used for the industrial development of formulations of sanitary, pharmaceutical and cosmetic products that, unlike conventional methods, it takes place in oily phase so that it is more simple and economical, having noted that, at least by the applicant, the existence of any document or invention that discloses a method for preserving and stabilising proteins or similar invention that has technical characteristics similar to those here proposed is unaware.

These and other objects and advantages of the present invention will become apparent from a reading of the attached specification and appended claims.

BRIEF SUMMARY OF THE INVENTION

The present invention is a method which involves the creation of a dispersed system as a means for preservation, stabilization and storage of proteins in an oily phase under normal pressure and temperature conditions. The method of the present invention is based on the incorporation of proteins, such as cell growth factors such as tales epidermal growth factor and fibroblast growth factor, in a medium composed of components, such as grape seed oil and a base including various components which form the oily phase. In particular, the method of the present invention takes advantage of some chemical groups of the oily phase components to promote certain physical-chemical interactions with the residues of proteins that enhance, for longer periods of time, the maintenance of the native molecular structure of proteins. The method is simple, economical and of general application. This method has the potential capacity to replace complex preservation techniques and/or aqueous means commonly used for the preservation of proteins.

In particular, this method for the preservation and stabilizing a proteins includes the steps of forming an anhydrous medium having oily phase components having hydrophilic residues; and dispersing the proteins into the anhydrous medium under ambient pressure and temperature conditions so that the proteins are incorporated into the anhydrous medium so as to maintain an active formation of the proteins. The oily phase components can comprise a base having caprylic/capric triglyceride, propylene glycol, pentaerythritol tetrakis (3-(3,5-di-tert-butyl-4-hydroxyphenol)) propionate, tocopherol, and triisopropanolamine, and grape seed oil.

This foregoing Section is intended to describe, with particularity, the preferred embodiment of the present invention. It is understood that modifications to this preferred embodiment can be made within the scope of the present claims. As such, this Section should not to be construed, in any way, as limiting of the broad scope of the present invention. The present invention should only be limited by the following claims and their legal equivalents.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
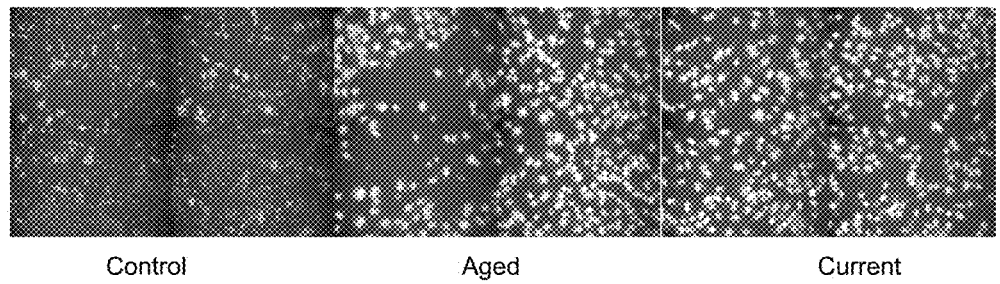
FIG. 1 shows the growing of epidermal cells obtained with a control and two formulations FO (aged and fresh, 5 ppm) in an in vitro assay.

A medium for dispersing proteins the components of which provides the medium with an oily character has been developed. Thus, KGF, EGF, FGF, TGF y etc. cell growth factors and/or proteins, as stated, are macromolecules with difficult stabilization, since, currently, the majority of dispersion means have an aqueous character and achieve the stabilization in a short period of time, through the use of dispersed systems, such as emulsions, or expensive and very specific methods that do not ensure a longer life of the protein native structure, such as lyophilization.

With the present invention, the development of the EGF and other growth factors and/or proteins has been carried out in an oily medium as an intermediate product for use in specific industrial processes, promoting the stability of proteins with respect to the currently existing methods thus achieving a more effective action to the non-denatured proteins in such medium not being denatured the proteins in such medium.

Regarding the manufacturing process, it consists in preparing the following phases as described below:

Mix grape seed oil, caprylic/capric triglyceride, PEG-18 castor oil dioleate, PEG/PPG-4/12 dimethicone and propylene glycol, and stir for some minutes. Then add pentaerythrityl tetra-di-T-butyl hydroxy hydrocinnamate, tocopherol, triisopropanolamine and butylhydroxytoluene, and stir for some minutes.

Prepare a different mixture of the protein, grape seed oil, caprylic/capric triglyceride, PEG-18 castor oil dioleate, PEG/PPG-4/12 dimethicone and propylene glycol, and stir for some minutes. Then add pentaerythrityl tetra-di-T-butyl hydroxy hydrocinnamate, tocopherol, triisopropanolamine, and stir for some minutes. Mix the two phases and stir for some minutes.

More specifically, according to the method of the present invention, in the formulation the growth factors are surrounded by an anhydrous medium composed of other components that act as adjuvants interacting with the residues of proteins, such components being: grape seed oil, that creates a medium which reduces the electrostatic interactions with the protein residues while maintaining the native conformation of the proteins; base consisting of: caprylic/capric triglyceride; a castor oil; a propylene glycol; a pentaerythrityl tetrakis (3-(3,5-di-tert-butyl-4-hydroxyphenol)) propionate, a tocopherol, a triisopropanolamine that promotes the interactions by intermolecular forces with the domains of proteins making the structure thermodynamically more stable.

The triisopropanolamine is an amine that is used in a variety of applications and, in particular, as an emulsifier and stabilizer. The triisopropanolamine is also used to neutralize some acidic components. The castor oil derived from the seed of the *Ricinus communis* plant and its primary constituent, ricin oleic acid, along with certain of its salts and esters function primarily as skin-conditioning agents, emulsion stabilizers, and surfactants in cosmetics, although other functions also occur. The castor oil can enhance the transdermal penetration of the other chemicals.

Note that the inter-position process of the protein with the oily phase components is carried out with appropriate quality. Such a process is preferably carried out in clean rooms, under laminar flow conditions, where environmental quality controls as well as microbiological controls are guaranteed to ensure the sterility of the product.

In short and succinctly, the present invention proposes the development of a method for the preservation, storage and stabilization of proteins which contemplates an anhydrous dispersion phase (i.e., in the absence of water) with environmental and microbiological quality, through the application of oily substances having hydrophilic residues that guarantee interactions with the proteins that keep its conformation in the native state, constituting a reproducible, simple and economic method with regard to others methods that require the use of devices, complex methods and qualified personnel.

EXAMPLES

Manufacturing Process

Regarding the manufacturing process, it consists in preparing the following phases as described below:

Mix grape seed oil, caprylic/capric triglyceride, PEG-18 castor oil dioleate, PEG/PPG-4/12 dimethicone and propylene glycol, and stir for some minutes. Then add pentaerythrityl tetra-di-T-butyl hydroxyhydrocinnamate, tocopherol, triisopropanolamine and butylhydroxytoluene, and stir for some minutes.

Prepare a different mixture of the protein, grape seed oil, caprylic/capric triglyceride, PEG-18 castor oil dioleate, PEG/PPG-4/12 dimethicone and propylene glycol, and stir for some minutes. Then add pentaerythrityl tetra-di-T-butyl hydroxy hydrocinnamate, tocopherol, triisopropanolamine, and stir for some minutes. Mix the two phases and stir for some minutes.

The amounts for the components and those related to the its use are listed in the following table 1:

TABLE 1

| Components | Concentration (% w/w) |
| --- | --- |
| BHT | ≤1 |
| Caprylic/capric triglyceride | >25-≤50 |
| PEG/PPG-4/12 dimethicone | >1-≤10 |
| PEG-18 Castor oil dioleate | >1-≤10 |
| Pentaerythrityl tetra-di-T-butyl hydroxyhydrocinnamate | ≤1 |
| Propylene glycol | ≤1 |
| tocopherol | ≤1 |
| Tocopheryl Acetate | ≤1 |

TABLE 1-continued

| Components | Concentration (% w/w) |
| --- | --- |
| Triisopropanolamine | ≤1 |
| *Vitis vinifera* seed oil | >25-≤50 |

Efficiency In Vitro

The efficiency in vitro of the formulation obtained from EGF dispersed in an anhydrous medium containing oily components having hydrophilic residues according to claim 1 was tested. Such formulation was assayed in an aged oily phase containing 5 ppm of EGF and an tapped ampule containing the oily phase and 5 ppm of EGF (fresh). The objective of the assay was to determine if the formulations were able to enhance the growing of epidermal cells and in which rate they did in relation to a control containing only the oily phase.

Epidermal cells were seeded at a 1M/plate in well plates with a final volume per well of 200 μl. The plates were incubated for 24 h at 37° C., 5% CO2 and 95% RH. The incubation medium was changed after 24 hours. The samples were tested in relation to the concentration, and the higher concentration was 10 μl of sample/200 μl of medium. Starting from this concentration, 30 μl+600 μl of medium was added and from this one dilutions ½ were obtained. 100 μl of such dilutions were disposed in corresponding columns for the test. The FIG. 1 shows the growing obtained with the control and the two formulations FO (aged and fresh, 5 ppm):

The mean values were as follows:
Control: 185 cells/well
Aged: 311 cells/well
Fresh: 380 cells/well As a conclusion, with these in vitro assays is showed that in wells with aged FO with 5 ppm of EGF the rate of growth was 68% in relation to the control, while with fresh FO with 5 ppm of EGF the rate was 105%.

Efficiency In Vivo

The formulation obtained according to the method of the present invention enhances the EGF activity with a topical application and preserve proteins during 3 years.

To show the efficiency in vivo, the preserved and stabilized protein product was used with patients suffering burns class II superficial and deep degree. The patient was treated with EGF oily phase, and the results are showed in FIG. 2.

Figure 3:
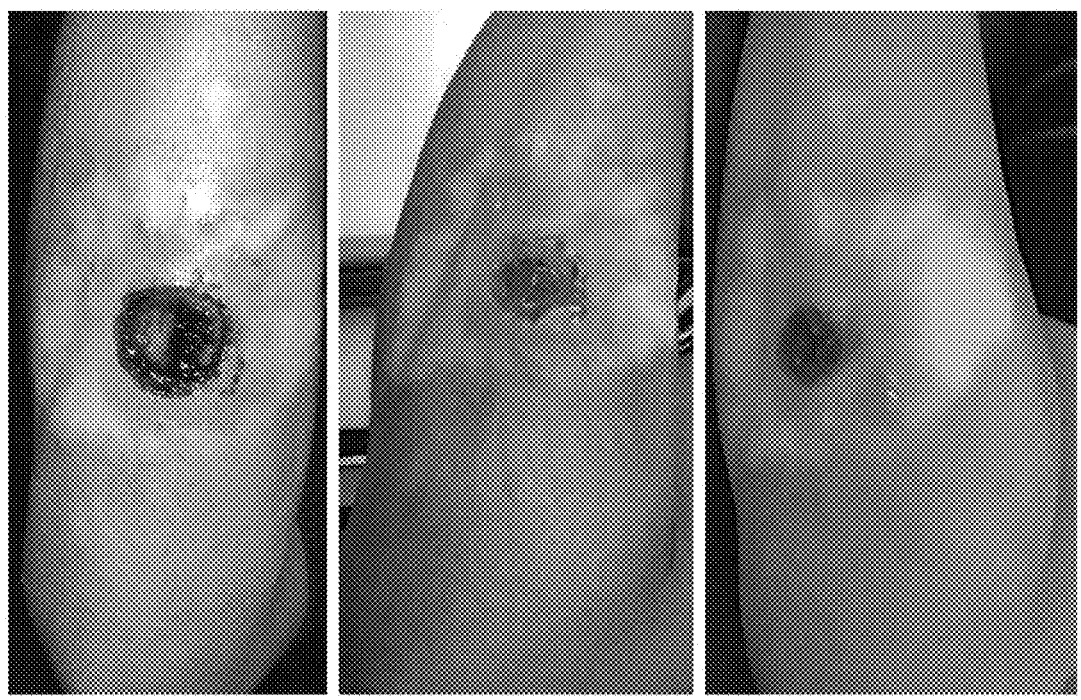
FIG. 3 is a set of photographs showing the efficiency in vivo of the EFG oily phase over chemical burns.

The same product was used to treat a patient suffering chemical burns, the results are showed in FIG. 3, and other kind of injuries (FIGS. 4-7).

Figure 2:
FIG. 2 is a set of photographs showing the efficiency in vivo of the EFG oily phase over burns class II, superficial and deep.

FIG. 2 is a set of photographs showing the efficiency in vivo of the EFG oily phase over burns class II, superficial and deep. The patient is a 26-year old male. The photos are taken over 3 weeks of treatment with EGF oily phase. Iconography and Protocol is courtesy of Drs. Marlen Cardenas and Ricardo Madiedo, plastic surgeons in the Burn Department of Simon Bolivar Hospital, Bogota.

FIG. 3 is a set of photographs showing the efficiency in vivo of the EFG oily phase over chemical burns. The patient is a 30-year old male. The chemical burn closure by second intention unstable scar that re-ulcer with mild trauma. Treatment time: 8 sessions. Iconography and Protocol courtesy of Drs. Marlen Cardenas and Ricardo Madiedo, plastic surgeons in the Burn Department of Simon Bolivar Hospital, Bogota.

Figure 4:
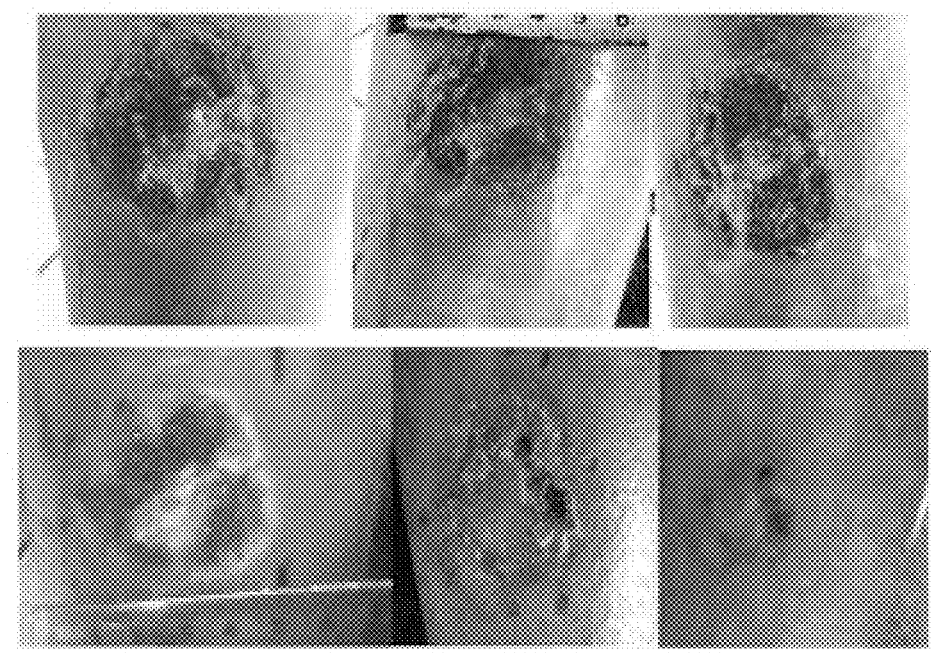
FIG. 4 is a set of photographs showing the efficiency in vivo of the EFG oily phase over diabetic ulcers after 30 days of treatment.

FIG. 4 is a set of photographs showing the efficiency in vivo of the EFG oily phase over diabetic ulcers after 30 days of treatment. The patient is a 70-year old woman. 8 months of evolution pathology. Results shown are after 30 days of treatment with EGF oily phase. Center Hohl medicina e diagnostico Brasil; Doctor Zelsa Teixeira Hohl. After 8 months with this wound, the patient finally had a totally closure of lesion thanks to EGF stable formulation.

Figure 5:
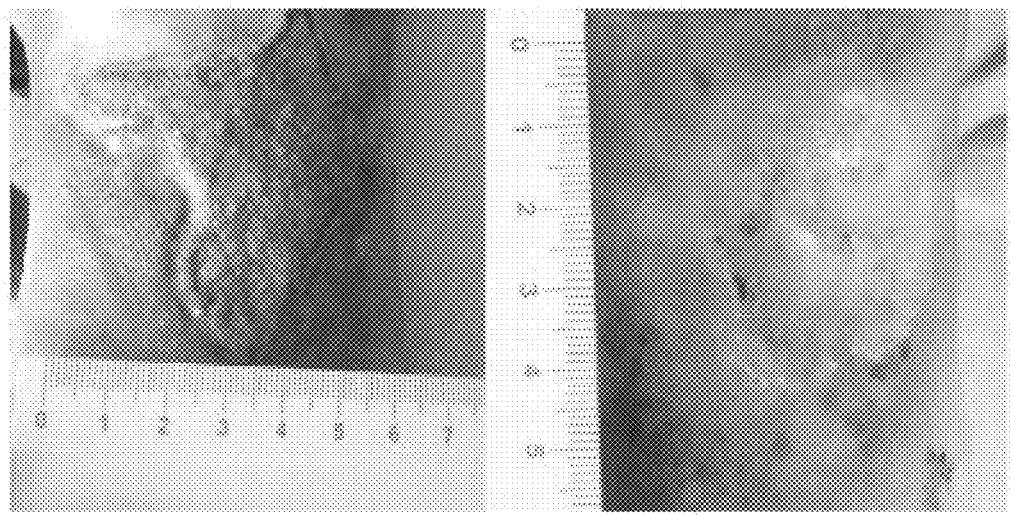
FIG. 5 is a set of photographs showing the efficiency in vivo of the EFG oily phase over venous ulcers after 40 days of treatment.
Figure 6:
FIG. 6 is a set of photographs showing the efficiency in vivo of the EFG oily phase over cut injuries after 44 days of treatment.

FIG. 5 is a set of photographs showing the efficiency in vivo of the EFG oily phase over venous ulcers after 40 days of treatment. The patient is a 35-year old woman. 4 years evolution pathology. University Federal de Campina Grande, nurse Lidiany Galdino Felix. There are not many formulations that are able to give this kind of results. The patient and nurse are totally satisfied FIG. 6 is a set of photographs showing the efficiency in vivo of the EFG oily phase over cut injuries after 44 days of treatment. The patient is a 66-year old male, who was cut with glass. Center: University Federal de Campina Grande, nurse Lidiany Galdino Felix. Treatment resulted in total closure of the lesion. Just with a very effective formula a patient could have this result.

Figure 7:
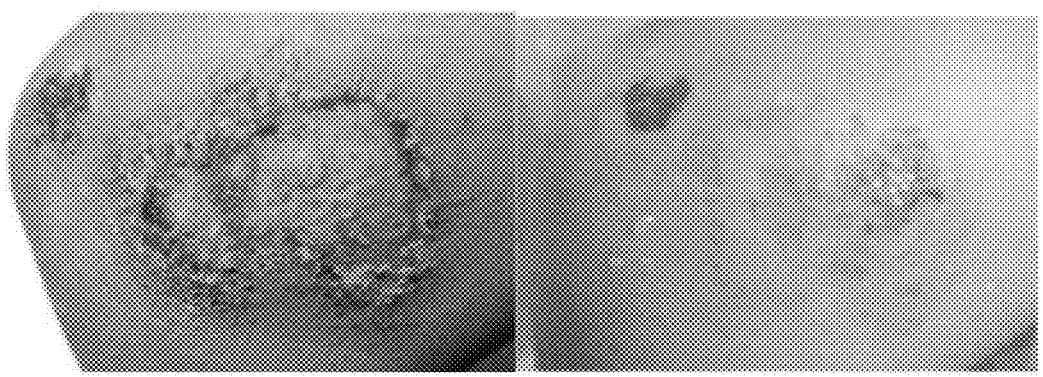
FIG. 7 is a set of photographs showing the efficiency in vivo of the EFG oily phase over second degree burns after 14 days of treatment.

FIG. 7 is a set of photographs showing the efficiency in vivo of the EFG oily phase over second degree burns after only 14 days of treatment. The patient is an 18-year old woman. Hospital Clinica Benalmadena, nurse Maria Jose Garcia Garcia.

Figure 8:
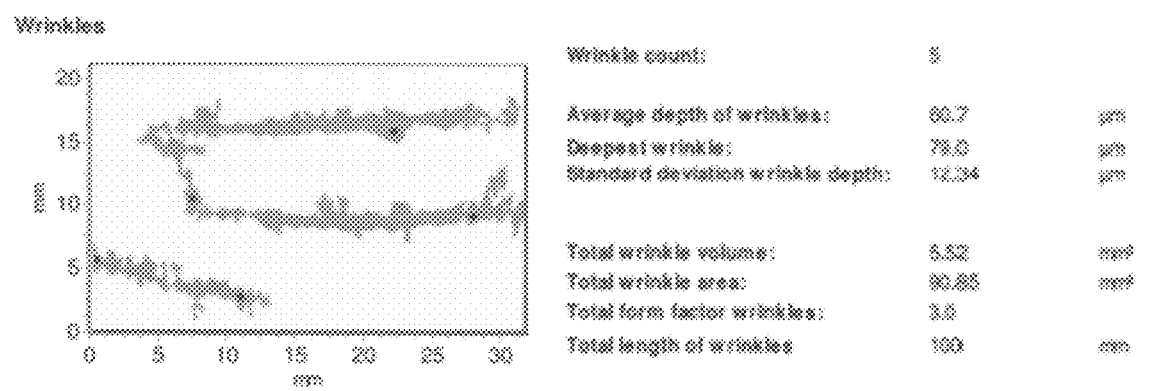
FIG. 8 are graphics showing the effect of the EFG oily phase in a formulation related to wrinkle reduction.
Figure 8:
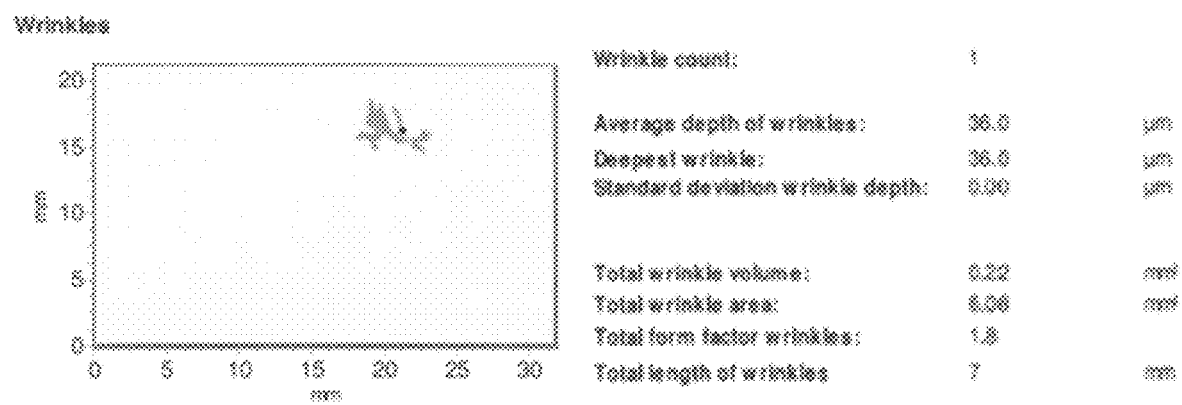

Other assays related to the total wrinkle volume were made in order to show the anti-aging effect of the formulation (FIG. 8). The total wrinkle volume decreases from 5.53 $mm^3$ to 0.22 $mm^3$ than means −96%. The total wrinkle area decreases from 90.85 $mm^2$ to 6.06 $mm^2$ than means −93%.

As a conclusion for these assays:
The cases treated with the formula are comparable with surgery treatments.
The treatments in some cases have changed life expectations since in other way they could loss limb.
The healing time for ulcers and burns is really fast.
The results as antiaging formula are possible with EGF stable and effective formulation and just without surgery.
It is possible to see results of the effectiveness of EGF oily phase. Just a stable protein can have this effectiveness.
The proposal formulation potentiates the activity of EGF once applied topically.
It allows to use concentrations ten times lower than those cited in bibliography.
It improves the conformity of the protein, making it stable and active for a longer time, since its useful life would be only 7 hours.

As it is derived from this assays, in particular from the in vitro assays, it can be concluded that the protein with a short mean life of 7 hours, in the aged and current formulations, preserves a great part of its efficiency. This preservation is accompanied by some effect over the protein configuration, as it is showed by results in vitro and in vivo with low concentrations of EGF (10 times less that those cited in literature).

So briefly, the formulation obtained by the method of the present invention enhances the EGF activity with a topical application and with levels of EGF very low in comparison with the formulations according to the prior art. It also enhances the protein conformation, making the EGF stable and active for longer (mean life is only 7 hours, as it is reported by Chih-Hui Yang, Yaw-Bin Huang, Pao-Chu Wu, Yi-Hung Tsai, "Process Biochemistry" Volume 40, Issue 5, April 2005, Pages 1661-1665. Based on the Arrhenius equation, the half-life of rhEGF at 25° C. was 6.93 h., available from https://www.sciencedirect.com/science/article/pii/S0032959204002638).

So, the hydrophilic residues make possible keeping the structure and conformation of the protein, in particular the native conformation or even a more active one. This can be showed by several assays wherein the efficacy of the proteins as they are obtained according to claim 1 has been investigate in base of the determination of the biochemical equivalence of the protein by in vitro activity and or preclinical in vivo assays.

The published studies give to EGF proteins a half-life of 7 hours, in this situation, reaffirms the novelty of our method of preparation, and our product, with a date of manufacture of more than one year, maintains all its effectiveness, superior to other products, in trials in vitro and in vivo:
growth of 40 to 200 fibroblasts cells starting from a single cell in two days, as it is showed before.
reduction of wrinkles of 90% that at 3 weeks the improvement is still greater than 30% (clinical trial published in Actual. Med. 2015).

The foregoing disclosure and description of the invention is illustrative and explanatory thereof. Various changes in the details of the steps of the described method can be made within the scope of the present claims without departing from the true spirit of the invention. The present invention should only be limited by the following claims and their legal equivalents.

BIBLIOGRAPHY

Chang L L, Pikal M J. Mechanisms of Protein Stabilization in the Solid State. J. Pharm. Sci. 98; 2009: 2886-2908.
Chi E Y, Krishnan S, Randolph T W, Carpenter J F. Physical stability of proteins in aqueous solution: mechanism and driving forces in nonnative protein aggregation. Pharm Res. 2003; 20: 1325-36.
Krishnamurthy R, Manning M C. The stability factor: importance in formulation development. Curr Pharm Biotechnol. 2002; 3: 361-71.
Schouest J M, Lun T K, Moy R L. Improved texture and appearance of barley produced, synthetic, human-like epidermal growth factor (EGF) serum. J. Drugs Dermatol. 2012; 11 (5): 613-620.
Tang Z, Zhang Z, Zheng Y et al. Cell aging of human diploid fibroblasts is associated with changes in responsiveness to epidermal growth factor and changes in HER-2 expression. Mechanisms of Ageing and Development 1994; 73 (1): 57-67.

I claim:
1. A method for preserving and stabilizing epidermal growth factor protein, the method comprising:
(A) mixing grape seed oil, caprylic/capric triglyceride, PEG-18 castor oil dioleate, PEG/PPG-4/12 dimethicone, and propylene glycol and stirring the resulting mixture;
(B) adding pentaerythrityl tetra-di-T-butyl hydroxy hydrocinnamate, tocopherol, triisopropanolarnine, and butylhydroxytoluene to the mixture of (A) and stirring the resulting mixture to form a first phase;
(C) mixing epidermal growth factor protein, grape seed oil, caprylic/capric triglyceride, PEG-18 castor oil dioleate, PEG/PPG-4/12 dimethicone, and propylene glycol and stirring the resulting mixture;
(D) adding pentaerythritol tetra-di-T-butylhydroxy hydocinnamate, tocopherol, and triisopropanolamine to the mixture of (C) and stifling the resulting mixture to form a second phase; and

(E) mixing the first phase of (B) with the second phase of (D) and stirring the resulting mixture, thereby preserving and stabilizing the epidermal growth factor protein.

\* \* \* \* \*